US011517695B2

(12) United States Patent
Mansfield et al.

(10) Patent No.: US 11,517,695 B2
(45) Date of Patent: Dec. 6, 2022

(54) ACOUSTICAL GUIDANCE AND MONITORING SYSTEM

(71) Applicant: Covidien LP, Mansfield, MA (US)

(72) Inventors: Jeffrey Mansfield, Bloomington, IN (US); Laura Lyons, Carmel, IN (US); Sven Schreiber, West Lafayette, IN (US); David Gunn, Katy, TX (US); Thomas Bumgardner, Roswell, GA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/858,239

(22) Filed: Apr. 24, 2020

(65) Prior Publication Data

US 2020/0384227 A1 Dec. 10, 2020

Related U.S. Application Data

(63) Continuation of application No. 15/081,847, filed on Mar. 26, 2016, now Pat. No. 10,668,240.

(60) Provisional application No. 62/138,840, filed on Mar. 26, 2015.

(51) Int. Cl.
*A61M 16/04* (2006.01)
*A61M 25/01* (2006.01)
(Continued)

(52) U.S. Cl.
CPC ......... *A61M 16/0488* (2013.01); *A61B 5/061* (2013.01); *A61M 16/0816* (2013.01);
(Continued)

(58) Field of Classification Search
CPC .......... A61M 16/0488; A61M 16/0003; A61M 16/0006; A61M 16/04; A61M 16/00; A61M 2205/3375; A61M 2205/14; A61M 2240/00; A61M 2039/1077; A61M 39/10; A61M 2230/40; A61B 5/0048;
(Continued)

(56) References Cited

U.S. PATENT DOCUMENTS 2,209,944 A 7/1940 Walker
4,344,436 A 8/1982 Kubota
(Continued)

FOREIGN PATENT DOCUMENTS

CN 1358548 7/2002
EP 1166813 1/2002
(Continued)

OTHER PUBLICATIONS

Boque, et al., Endotracheal tube intraluminal diameter narrowing after mechanical ventilation: use of acoustic reflectometry, Springer-Verlarg, Intensive Care Med, 2004, 30:2204-09.
(Continued)

*Primary Examiner* — Justine R Yu
*Assistant Examiner* — Matthew D Ziegler

(57) ABSTRACT

An apparatus for acoustically detecting the location of a distal end of a tube relative to a body conduit into which the tube is being inserted is provided. The apparatus including a speaker positioned to generate a sound pulse in the tube and a sensor for detecting a sound pulse in the tube at a distal position relative to the speaker, and for generating a signal corresponding to the detected sound pulse.

20 Claims, 12 Drawing Sheets

(51) Int. Cl.
  *A61B 5/06* (2006.01)
  *A61M 16/08* (2006.01)
  *A61M 25/00* (2006.01)

(52) U.S. Cl.
  CPC ............ *A61M 25/01* (2013.01); *A61M 25/00* (2013.01); *A61M 2205/14* (2013.01); *A61M 2205/3375* (2013.01); *A61M 2240/00* (2013.01)

(58) Field of Classification Search
  CPC ....... A61B 5/0051; A61B 5/68; A61B 5/6846; A61B 5/6847; A61B 5/6852; A61B 7/003; A61B 7/00; A61B 2010/0083; A61B 2010/0087; A61B 2560/0406; A61B 2560/0456; A61B 2562/0204; A61B 2562/0247; A61B 2562/166; A61B 2562/18
  USPC ... 73/1.82, 1.85, 1.88, 24.06, 586, 587, 589, 73/627, 628, 666, 861.26–861.31
  See application file for complete search history.

(56) References Cited

U.S. PATENT DOCUMENTS

| | | | |
|---|---|---|---|
| 4,501,273 A | 2/1985 | McGinnis | |
| 4,630,606 A | 12/1986 | Weerda | |
| 4,697,593 A | 10/1987 | Evans | |
| 4,700,396 A | 10/1987 | Bolin | |
| 4,757,821 A * | 7/1988 | Snyder | A61B 8/12 600/463 |
| 5,135,490 A | 8/1992 | Strickland | |
| 5,331,967 A | 7/1994 | Akerson | |
| 5,445,144 A | 8/1995 | Wodicka | |
| 5,575,310 A | 11/1996 | Kamen | |
| 5,655,518 A | 8/1997 | Burden | |
| 5,666,960 A | 9/1997 | Fredberg | |
| 5,727,549 A * | 3/1998 | Suda | A61B 5/113 600/393 |
| 5,823,965 A | 10/1998 | Rasmussen | |
| 5,829,429 A | 11/1998 | Hughes | |
| 5,853,005 A | 12/1998 | Scanlon | |
| 6,257,234 B1 | 7/2001 | Sun | |
| 6,390,091 B1 | 5/2002 | Banner | |
| 6,443,907 B1 | 9/2002 | Mansy | |
| 6,629,527 B1 | 10/2003 | Estes | |
| 6,705,319 B1 | 3/2004 | Wodicka | |
| 6,761,693 B1 | 7/2004 | Rasmussen | |
| 7,347,824 B2 | 3/2008 | Wilkinson et al. | |
| 7,691,070 B2 | 4/2010 | Comanducci | |
| 7,708,697 B2 | 5/2010 | Wilkinson et al. | |
| 7,850,618 B2 | 12/2010 | Wilkinson et al. | |
| 7,891,354 B2 | 2/2011 | Farbarik | |
| 8,038,629 B2 | 10/2011 | Solanki | |
| 8,152,751 B2 | 4/2012 | Roger | |
| 8,280,489 B2 | 10/2012 | Li | |
| 8,371,303 B2 | 2/2013 | Schaner | |
| 8,394,031 B2 | 3/2013 | Mansy | |
| 8,424,529 B2 | 4/2013 | Efrati | |
| 8,489,342 B2 * | 7/2013 | Dugger | G01F 1/66 702/48 |
| 8,522,787 B2 | 9/2013 | Lin | |
| 8,608,658 B2 | 12/2013 | Burbank | |
| 8,611,984 B2 | 12/2013 | Greenburg | |
| 8,764,725 B2 | 7/2014 | Averbuch | |
| 8,844,534 B2 | 9/2014 | Behlmaier | |
| 8,905,029 B2 | 12/2014 | Colburn | |
| 9,265,904 B2 * | 2/2016 | Esnouf | A61M 16/04 |
| 9,364,180 B2 | 6/2016 | Armitstead | |
| 9,498,590 B2 | 11/2016 | Mansfield | |
| 9,677,555 B2 * | 6/2017 | Kamen | F04B 49/00 |
| 9,707,363 B2 | 7/2017 | Mansfield | |
| 9,826,956 B2 * | 11/2017 | Freeman | A61M 16/0488 |
| 10,264,995 B2 * | 4/2019 | Brister | A61B 5/6861 |
| 10,729,621 B2 | 8/2020 | Mansfield et al. | |
| 10,780,238 B2 | 9/2020 | Efrati et al. | |
| 2001/0004893 A1 | 6/2001 | Biondi | |
| 2002/0016610 A1 | 2/2002 | Hovanes | |
| 2003/0018276 A1 | 1/2003 | Mansy | |
| 2003/0034035 A1 | 2/2003 | Raphael | |
| 2004/0039294 A1 | 2/2004 | Sullivan | |
| 2005/0005935 A1 | 1/2005 | Gradon | |
| 2006/0032286 A1 * | 2/2006 | Magane | G01H 5/00 73/1.82 |
| 2006/0070623 A1 | 4/2006 | Wilkinson | |
| 2006/0070624 A1 | 4/2006 | Kane | |
| 2006/0081255 A1 | 4/2006 | Miller | |
| 2006/0107962 A1 | 5/2006 | Ward | |
| 2007/0137652 A1 | 6/2007 | Qureshi | |
| 2007/0257788 A1 | 11/2007 | Carlson | |
| 2008/0078248 A1 | 4/2008 | Farbarik | |
| 2008/0078390 A1 | 4/2008 | Milne | |
| 2009/0025728 A1 | 1/2009 | Aljuri | |
| 2009/0082676 A1 | 3/2009 | Bennison | |
| 2009/0099479 A1 | 4/2009 | Solanki | |
| 2009/0120439 A1 | 5/2009 | Goebel | |
| 2009/0187164 A1 | 7/2009 | Rowe | |
| 2009/0229605 A1 | 9/2009 | Efrati | |
| 2009/0229611 A1 | 9/2009 | Martin | |
| 2009/0301601 A1 | 12/2009 | Enerson | |
| 2009/0318805 A1 | 12/2009 | Raphael | |
| 2010/0101573 A1 | 4/2010 | Foley | |
| 2010/0252048 A1 | 10/2010 | Young | |
| 2010/0261996 A1 | 10/2010 | Li | |
| 2010/0317956 A1 | 12/2010 | Kartush | |
| 2011/0030694 A1 | 2/2011 | Schaner | |
| 2011/0087123 A9 | 4/2011 | Choncholas | |
| 2011/0154241 A1 | 6/2011 | Skidmore | |
| 2011/0197885 A1 | 8/2011 | Wondka | |
| 2011/0197888 A1 | 8/2011 | Deutsch | |
| 2011/0313689 A1 | 12/2011 | Holley | |
| 2012/0017700 A1 * | 1/2012 | Wiest | G01F 1/662 73/861.28 |
| 2012/0083702 A1 | 4/2012 | Ingold, Jr. | |
| 2012/0132211 A1 | 5/2012 | Halperin | |
| 2012/0215074 A1 | 8/2012 | Krimsky | |
| 2012/0232411 A1 | 9/2012 | Brunner | |
| 2013/0098363 A1 | 4/2013 | Forte | |
| 2013/0228171 A1 | 9/2013 | Mansfield | |
| 2013/0255691 A1 | 10/2013 | Mansfield | |
| 2013/0281885 A1 | 10/2013 | Rowbottom | |
| 2014/0051989 A1 | 2/2014 | McGowan | |
| 2014/0058253 A1 | 2/2014 | Prough | |
| 2014/0155720 A1 * | 6/2014 | Stanislaus | A61B 5/07 600/373 |
| 2014/0249428 A1 | 9/2014 | Ingold, Jr. | |
| 2014/0366874 A1 | 12/2014 | Deutsch | |
| 2017/0043110 A1 | 2/2017 | Mansfield | |
| 2017/0281887 A1 | 10/2017 | Mansfield | |
| 2017/0340522 A1 | 11/2017 | Mansfield | |
| 2019/0038862 A1 | 2/2019 | Mansfield | |

FOREIGN PATENT DOCUMENTS

| | | |
|---|---|---|
| EP | 1447048 | 8/2004 |
| JP | 2012517303 | 8/2012 |
| WO | 0006019 | 2/2000 |
| WO | 2009149351 | 12/2009 |
| WO | 2009155515 | 12/2009 |
| WO | 2010091462 | 8/2010 |
| WO | 2010141415 | 12/2010 |
| WO | 2011115838 | 9/2011 |
| WO | 2013134166 | 9/2013 |
| WO | 2013149138 | 10/2013 |
| WO | 2016154607 | 9/2016 |

OTHER PUBLICATIONS

Co-pending U.S. Appl. No. 15/610,360, filed May 31, 2017.
Co-pending U.S. Appl. No. 16/054,734, filed Aug. 3, 2018.
Extended European search report and opinion dated Nov. 17, 2015 for EP Application No. 13770312.0.

(56) References Cited

OTHER PUBLICATIONS

Fiastro, et al., Pressure Support Compensation for Inspiratory Work due to Endotracheal Tubes and Demand Continuous Positive Airway Pressure, Chest, Mar. 1988, 93(3):499-505.
International Preliminary Report on Patentability written opinion dated Jul. 11, 2013 for PCT Application No. US-2013034599.
International Preliminary Report on Patentability written opinion, International search report and written opinion dated Jun. 24, 2016 for PCT Application No. US-2016024380.
International search report and written opinion dated Jul. 9, 2013 for PCT Application US2013028957.
International Search Report and Written Opinion for PCT/US2017/035299, 17 pages (Aug. 10, 2017).
Marshall, I., et al., "Acoustic reflectometry for airway measurements in man: implementation and validation," Physiological Measurement, Institute of Physics Publishing, Bristol, GB, vol. 14, No. 2, May 1, 1993.
Notice of allowance dated Mar. 10, 2017 for U.S. Appl. No. 13/853,252.
Notice of allowance dated Jul. 21, 2016 for U.S. Appl. No. 13/783,916.
Office action dated Feb. 4, 2016 for U.S. Appl. No. 13/853,252.
Office action dated Jun. 11, 2015 for U.S. Appl. No. 13/783,916.
Office action dated Aug. 15, 2016 for U.S. Appl. No. 13/853,252.
Office action dated Aug. 27, 2015 for U.S. Appl. No. 13/853,252.
Office action dated Nov. 25, 2015 for U.S. Appl. No. 13/783,916.
Schumann, et al., Detection of partial endotracheal tube obstruction by forced pressure oscillations, Respiratory Physiology & Neurobiology 155 (2007), 227-233.
U.S. Appl. No. 15/336,186 Notice of Allowance dated Apr. 27, 2018.
U.S. Appl. No. 17/198,818, filed Mar. 11, 2021, Gardner J. Kimm.
New Zealand Examination Report for Application No. 735447 dated Feb. 23, 2022 (6 pages).

* cited by examiner

ACOUSTICAL GUIDANCE AND MONITORING SYSTEM

BACKGROUND

Endotracheal tubes (hereinafter "ETTs"), often referred to as breathing tubes, are used to provide a conduit for mechanical ventilation of patients with respiratory or related problems. An ETT is inserted through the mouth or nose and into the trachea of a patient for several reasons: (1) to establish and maintain an open airway; (2) to permit positive pressure ventilation which cannot be done effectively by mask for more than brief periods; (3) to seal off the digestive tract from the trachea thereby preventing inspiration of forced air into the stomach; and (4) as an anesthesia delivery system. For example, U.S. Pat. No. 6,705,319 describes an acoustic reflectometry device for tubes and catheters, including endotracheal tubes, and includes a sound pulse generator and two or more sound pulse receivers that constitute the reflectometry device.

The size and complexity of known reflectometry devices limit their use and effectiveness with many patients, especially neonatal patients. Accordingly, there is a need for an apparatus being configured to efficiently assist in the proper placement of ETTs and other tubes. Further, there exists a need for an apparatus being configured to efficiently assist in the proper placement of ETTs and other tubes in neonatal patients.

SUMMARY OF THE DISCLOSED EMBODIMENTS

The present disclosure relates to apparatuses for acoustically guiding, positioning, and monitoring a tube or catheter within a body. More particularly, the present disclosure relates to apparatuses to guide the placement of a tube in a body conduit or cavity, to monitor the position of the tube, and to ensure the patency of the tube in the body using a noninvasive acoustic technique.

In at least one embodiment, the present disclosure includes disclosure of an apparatus for detecting acoustic reflections that arise from within a tube and body conduit, the tube having a proximal end and a distal end, the apparatus coupled to the proximal end, the distal end of the tube inserted into the body conduit, the apparatus comprising a sound generator positioned to generate a sound signal in the tube; a sensor for detecting a sound signal in the tube at a distal position relative to the sound generator, and for generating a signal corresponding to the detected sound signal; and a housing including the sound generator and the sensor and having a tube connector sized for connection to a neonatal endotracheal tube. In an aspect of at least one such embodiment of the present disclosure, the housing includes a first housing member coupled to a second housing member, the sound generator being positioned in the first housing and the sensor being positioned in the second housing. In an aspect of at least one such embodiment of the present disclosure, the first housing member is coupled to the second housing member to define an internal volume. In an aspect of at least one such embodiment of the present disclosure, the sensor includes a piezo-electric film. In an aspect of at least one such embodiment of the present disclosure, the apparatus for detecting acoustic reflections comprises a compliant tube aligned with the sensor and configured to transmit sound pressure waves from within the compliant tube to the sensor. In an aspect of at least one such embodiment of the present disclosure, the sensor is wrapped at least partially around the compliant tube. In an aspect of at least one such embodiment of the present disclosure, the sensor contains at least two sensing elements that are spaced apart and aligned with the compliant tube. In an aspect of at least one such embodiment of the present disclosure, the apparatus for detecting acoustic reflections comprises an adjustment member aligned with the first sensing element, wherein the adjustment member is configured to adjust a mean pressure applied to the first sensing element. In an aspect of at least one such embodiment of the present disclosure, the apparatus for detecting acoustic reflections comprises a second adjustment member aligned with the second sensing element, wherein the second adjustment member is configured to adjust a mean pressure applied to the second sensing element. In an aspect of at least one such embodiment of the present disclosure, the tube connector has an inner diameter no greater than about 3.5 mm. In an aspect of at least one such embodiment of the present disclosure, the housing further includes a device fitting, the sound generator being axially aligned within the device fitting.

In at least one embodiment, the present disclosure includes disclosure of an apparatus for detecting acoustic reflections that arise from within a tube and body conduit, the tube having a proximal end and a distal end, the apparatus coupled to the proximal end, the distal end of the tube inserted into the body conduit, the apparatus comprising a sound generator positioned to generate a sound signal in the tube; a sensor for detecting a sound signal in the tube at a distal position relative to the sound generator, and for generating a signal corresponding to the detected sound signal; and a compliant tube aligned with the sensor and configured to transmit sound pressure waves from within the compliant tube to the sensor. In an aspect of at least one such embodiment of the present disclosure, the sensor includes a piezo-electric film. In an aspect of at least one such embodiment of the present disclosure, the sensor contains at least two sensing elements that are spaced apart and aligned with the compliant tube. In an aspect of at least one such embodiment of the present disclosure, the apparatus for detecting acoustic reflections further comprises an adjustment member aligned with the first sensing element, wherein the adjustment member is configured to adjust a mean pressure applied to the sensing element. In an aspect of at least one such embodiment of the present disclosure, the adjustment member includes a set screw and adjustment plate, wherein rotation of the set screw deflects the adjustment plate toward the sensor. In an aspect of at least one such embodiment of the present disclosure, the adjustment member further includes a compliant sheet disposed between the adjustment plate and the sensor such that deflection of the adjustment plate toward the sensor applies pressure to the compliant sheet and the sensing element. In an aspect of at least one such embodiment of the present disclosure, the apparatus for detecting acoustic reflections further comprises a second adjustment member aligned with the second sensing element, wherein the second adjustment member is configured to adjust a mean pressure applied to the second sensing element. In an aspect of at least one such embodiment of the present disclosure, the sensor directly contacts the compliant tube. In an aspect of at least one such embodiment of the present disclosure, the sensor is wrapped at least partially around the compliant tube.

In at least one embodiment, the present disclosure includes disclosure of an apparatus for detecting acoustic reflections that arise from within a tube and body conduit, the tube having a proximal end and a distal end, the apparatus coupled to the proximal end, the distal end of the tube inserted into the body conduit, the apparatus comprising a sound generator positioned within the ventilator or at a distal position to the ventilator within the breathing circuit to generate a sound signal into a sensor distal to the sound generator; a sensor for detecting a sound signal in the tube at a distal position relative to the sound generator, and for generating a signal corresponding to the detected sound signal; and a housing including the sensor and having a tube connector sized for connection to an endotracheal tube.

In at least one embodiment, the present disclosure includes disclosure of a method of synchronizing collection of an acoustic reflectometry signal with a phase of a respiratory cycle, comprising the steps of sensing a ventilation pressure signal; determining a phase of a respiratory cycle based on the ventilation pressure signal; establishing a collection period based on a beginning and an end of the phase; and collecting one or more acoustic reflectometry signals during the collection period.

BRIEF DESCRIPTION OF THE DRAWINGS

The embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein.

DETAILED DESCRIPTION OF THE DISCLOSED EMBODIMENTS

Figure 1:
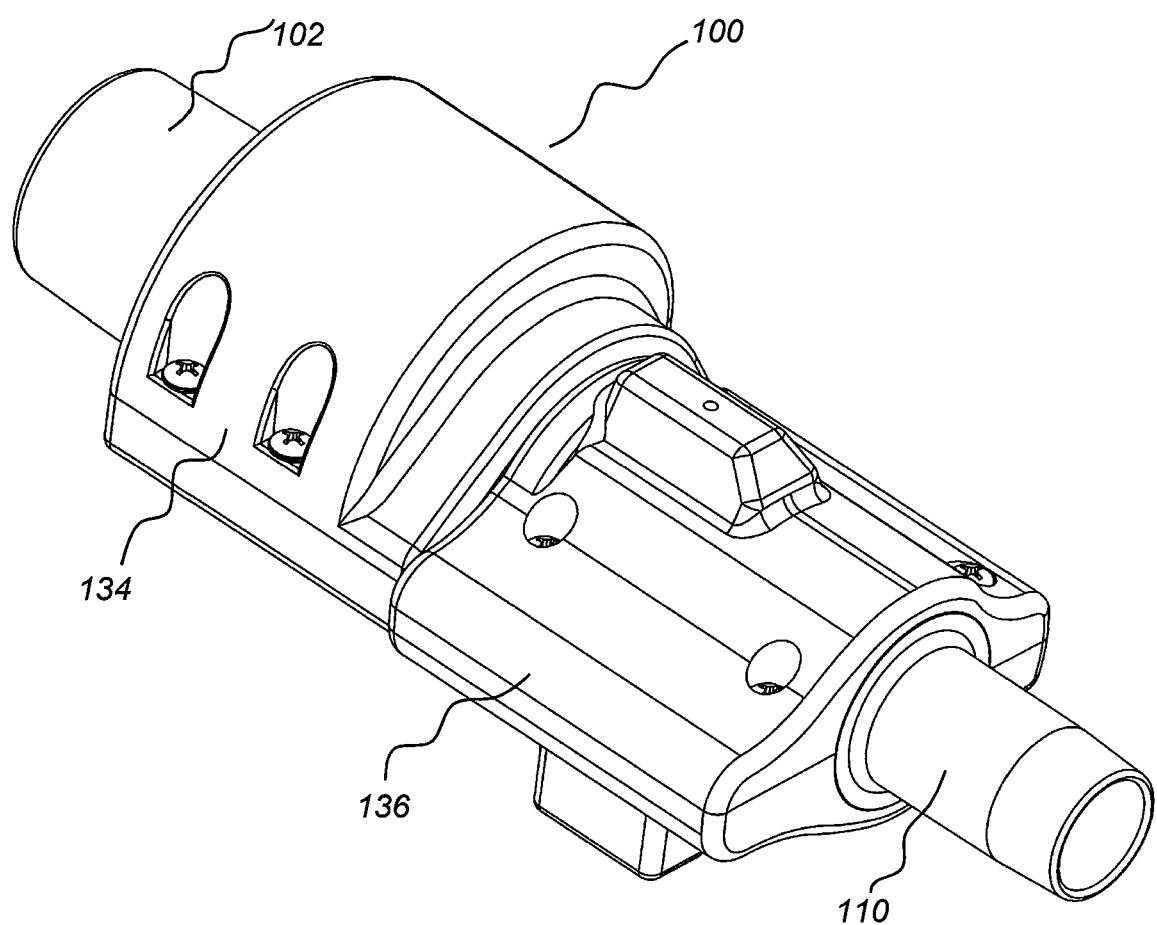
FIG. 1 illustrates a perspective view of an acoustic reflectometry device according to an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 2:
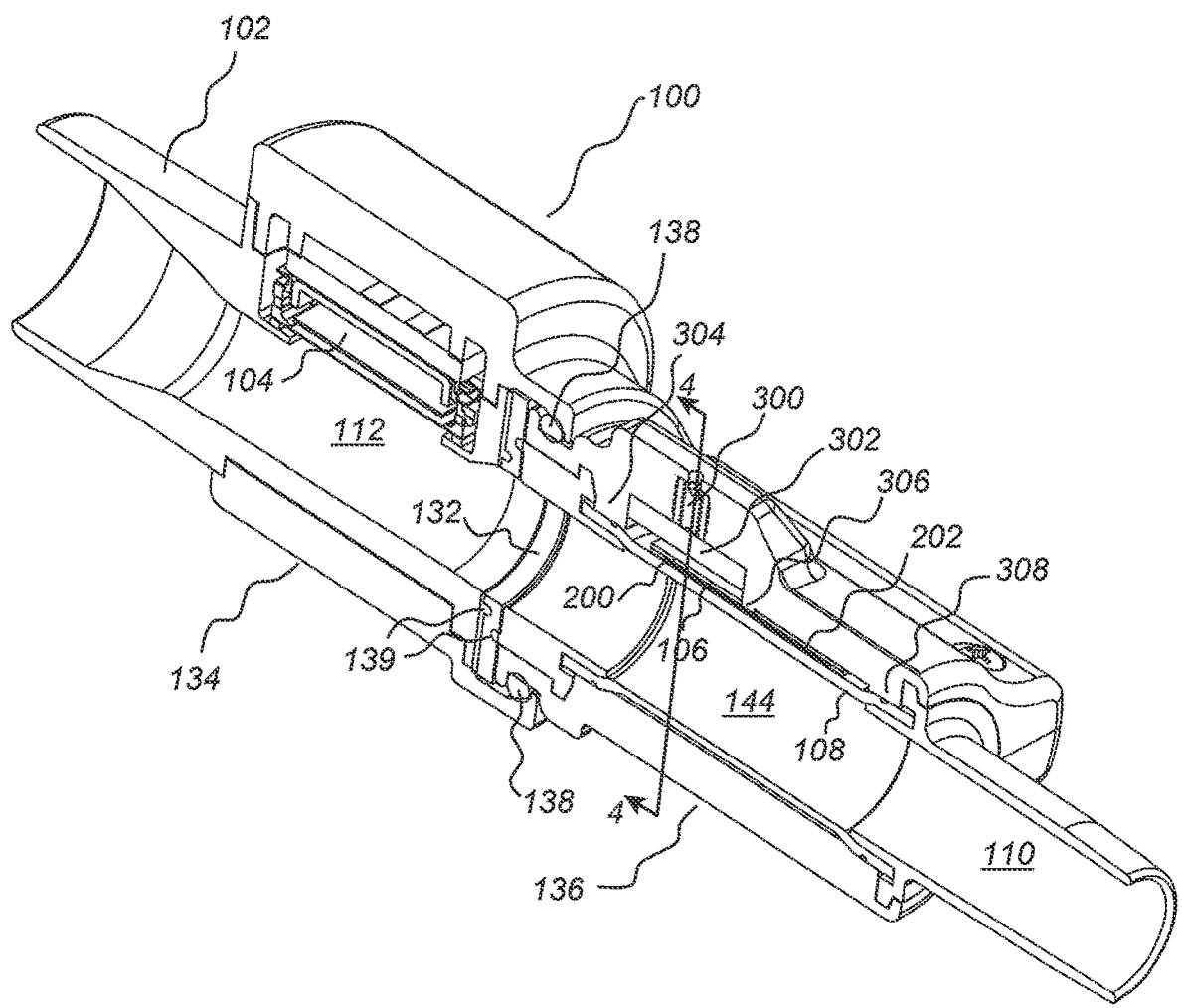
FIG. 2 illustrates a cross sectional view of an acoustic reflectometry device according to an embodiment of the present disclosure.

Referring now to FIGS. 1 and 2, one embodiment of an acoustic reflectometry device 100 is shown for large endotracheal tubes, such as those having an inner diameter (ID) between 5.5 mm and 9.0 mm. The device 100 contains a 15 mm outer diameter airway device fitting 102 for connection to a ventilator hose or other ventilation device, such as a closed circuit suction catheter, flow sensor, filter, or humidifier, a sound generator or speaker 104 for generating sound pulses, a sensor, including the non-limiting example of a vibration sensing piezo-electric film 106, for sensing acoustic pressure waves that arise from within a compliant walled tube 108, and a nozzle 110 of specified inner diameter for connection to an ETT having a complimentary ID. In one embodiment, the device 100 illustrated in FIGS. 1 and 2 has an approximate length of 8.5 cm, which is considerable for use in neonates.

Figure 3:
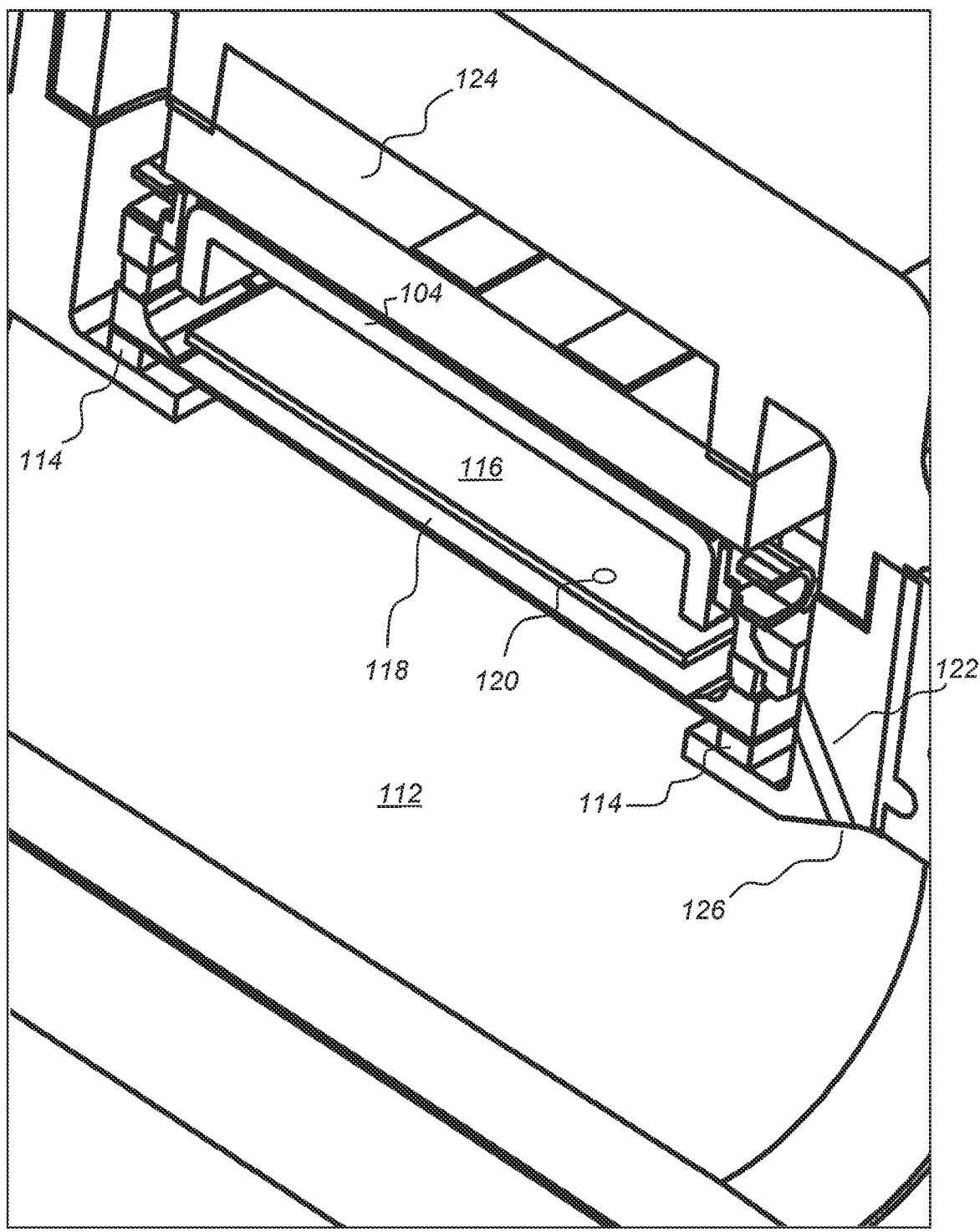
FIG. 3 illustrates an enlarged cross sectional view of an acoustic reflectometry device according to an embodiment of the present disclosure.

Referring now to FIG. 3, the speaker 104 is configured to be coupled to a lumen 112 of the acoustic reflectometry device 100 with a gasket 114 to provide both a pressure and acoustic seal between a speaker diaphragm 116 and the lumen 112. To reduce the loading effects on the speaker diaphragm 116 from the positive pressures developed within the lumen 112 during positive pressure ventilation, a non-porous, compliant, thin membrane 118 is situated between the speaker diaphragm 116 and the lumen 112 in one embodiment. The membrane 118 should be sufficiently taut as to not be deflected by the positive pressures to an extent that it comes in contact with the speaker diaphragm 116 and with thickness and compliance selected to provide an acoustic transmission response of as close to unity gain as possible over the frequency band of the excitation signal (e.g. 100-15,000 Hz in this case). The membrane 118 also serves to provide a barrier to prevent fluids from within the lumen 112, such as mucus, water, or blood, from accumulating on, and thereby loading, the speaker diaphragm 116. This allows the frequency response of the speaker 104 to be relatively insensitive to accumulation of fluids on the membrane 118. In an embodiment where the back of the speaker 104 is not hermetically sealed, a shunt 120, including as one non-limiting example a pin hole, is provided between front and back surfaces of the speaker diaphragm 116 such that the sealed cavity formed between the speaker diaphragm 116 and the membrane 118 is equalized to atmospheric pressure.

One embodiment of the device 100 includes a cavity shunt 122 between the lumen 112 and the speaker back cavity 124 to equalize the pressure between the front and back of the speaker diaphragm 116 and to eliminate the loading effect of positive pressures on the speaker diaphragm 116. In this embodiment, the back cavity 124 is hermetically sealed and a non-porous membrane 126 placed across the opening of the shunt 122 to prevent ingress of fluids into the back cavity 124. The compliance and surface area of the membrane 126 is selected in an embodiment to allow it to deflect adequately to equalize the pressures on either side. A further embodiment replaces the membrane 126 with a mechanism that provides a functional equivalent of the membrane by equalizing the pressure between the lumen 112 and the speaker back cavity 124 and preventing ingress of fluids (and water vapor) into the back cavity 124.

In an embodiment, the volume of the speaker back cavity 124 is selected per the specification of the speaker manufacturer to provide the desired acoustical response from the speaker 104.

Referring back to FIG. 2, an annulus ring 132 composed of a highly compliant, viscoelastic material, such as a Shore 35A durometer hardness silicone rubber in one non-limiting example, is situated between the device's speaker (sound generating) section 134 and the sensor (sound receiving) section 136 to dampen the vibrations that may be transmitted through the body of the speaker section 134 to the sensor section 136. This vibration isolation between the two sections 134, 136 prevents secondary (undesired) vibrations from being transmitted through the speaker section body 134 to the vibration sensing piezo-electric film 106 that may interfere with the primary (desired) vibrations sensed by the piezo-electric film 106 caused by sound waves from within the compliant-walled tube 108.

The speaker and sensor sections 134, 136, and sound dampening annular ring 132, are held together in an embodiment with an O-ring 138 selected to have a compliance that also provides vibration dampening functionality similar to the annular ring 132. The speaker and sensor sections 134, 136 are configured to provide a force that pulls each section toward the other with the O-ring 138 in compression between the sections in one embodiment. An equal and opposite force is provided by the annular ring 132 that is in compression. The compression of the annular ring 132 by beads 139 situated around the circumference of the mating faces provides a seal to maintain pressure within the lumen 112 during positive pressure ventilation.

The interior of the compliant-walled tube 108 forms the sensor tube lumen 144 through which the patient is ventilated and the sound waves travel to and from an ETT and a patient. The tube wall thickness and compliance are selected to provide adequate radial expansion and contraction of the tube wall in response to the sound pressure waves inside the tube to effectively transmit the sound pressure waves to the piezo-electric film 106 that is in contact with exterior of the sensor tube 108. A non-limiting example of a suitable wall thickness is between 0.5 mm and 1.0 mm and a material hardness of Shore 35A durometer. This configuration of a sound sensing element, such as the piezo-electric film 106, sensing sound waves from within the sensor tube lumen 144 provides a sound sensing means that is not confounded by fluids such as mucus, water, and blood. The transmission of sound pressure waves within the lumen 144 is largely unaffected by deposition and accumulation of fluids onto the interior walls on the lumen 144 since the pressures within are transmitted radially through these accumulated fluids.

Figure 4:
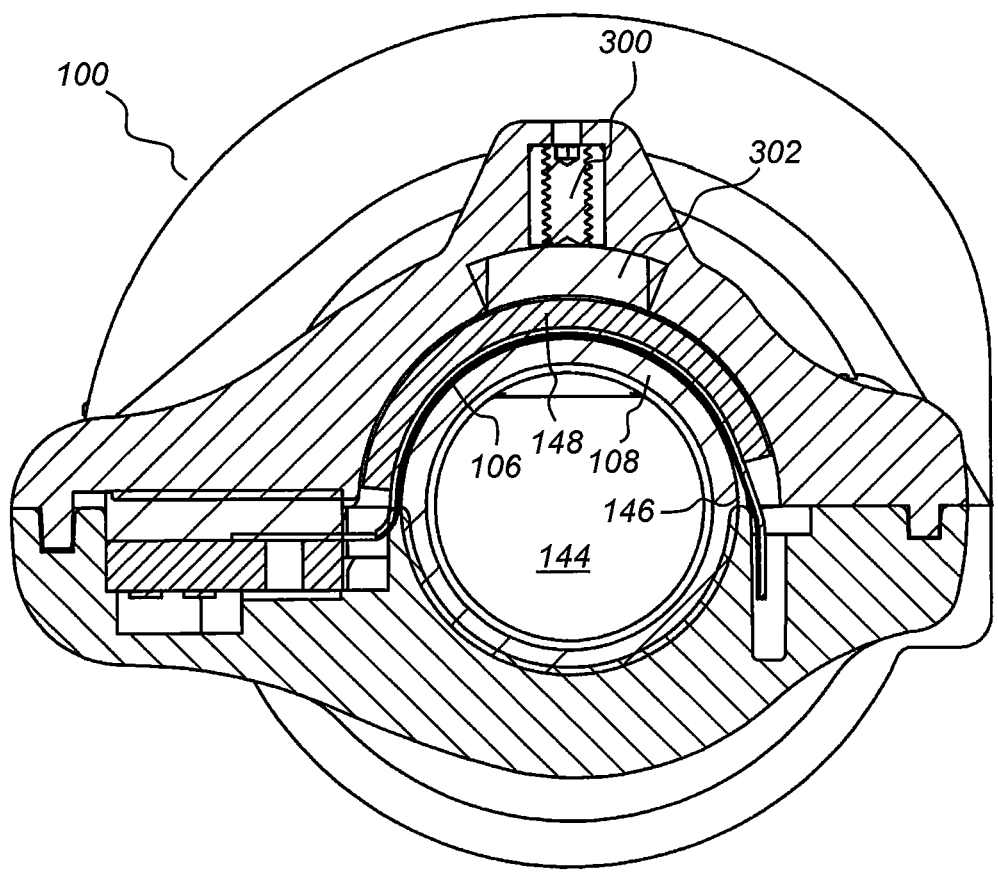
FIG. 4 illustrates a cross sectional view of an acoustic reflectometry device according to an embodiment of the present disclosure.
Figure 5A:
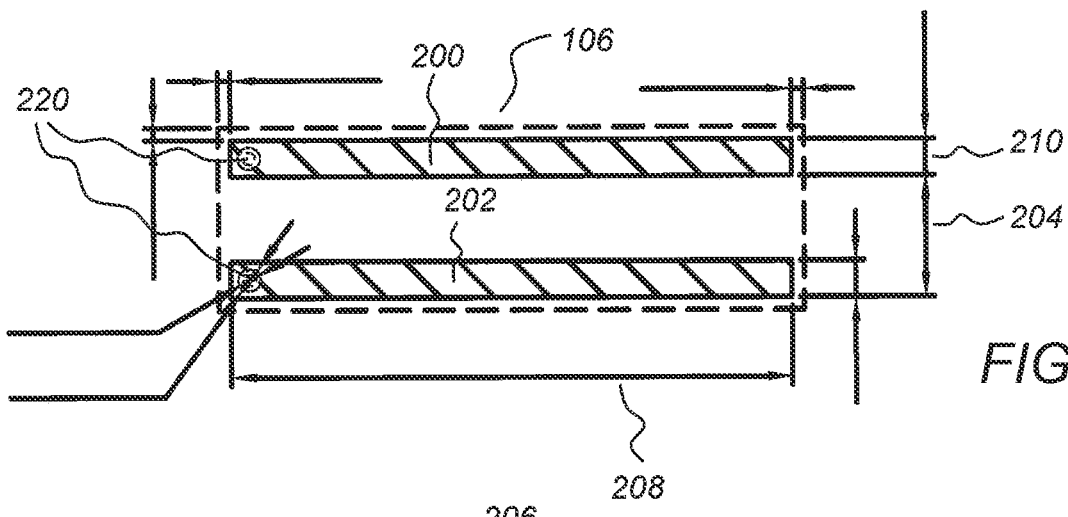
FIGS. 5A, 5B, 5C, and 5D illustrate plan views of sensors of acoustic reflectometry devices according to an embodiment of the present disclosure.
Figure 5B:
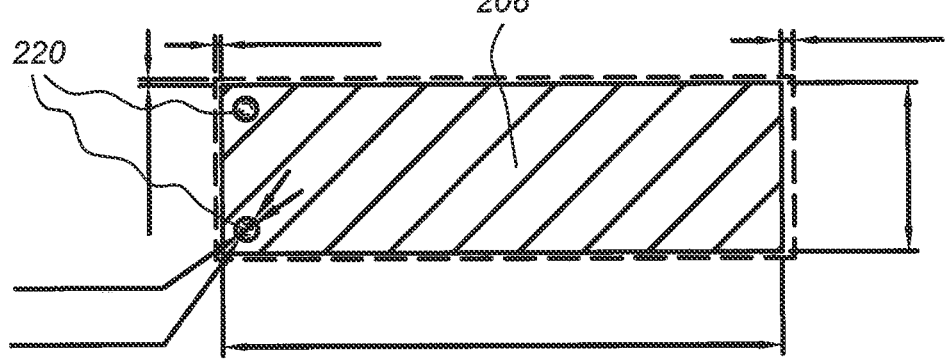
Figure 5C:
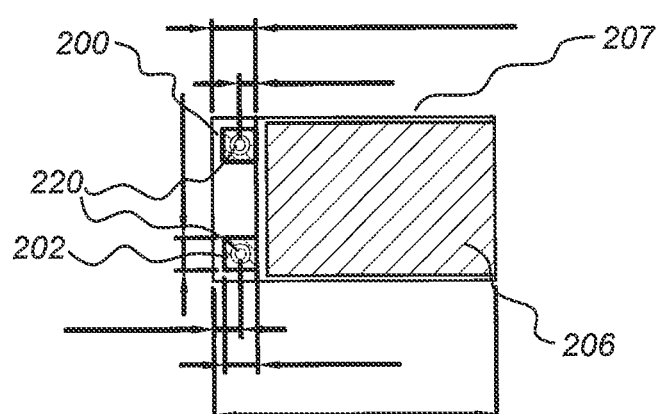
Figure 5D:
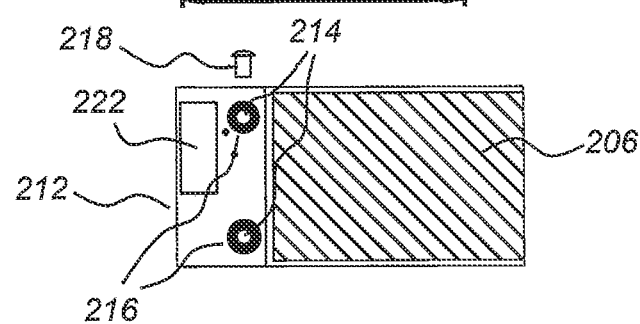

As shown in FIG. 4, the piezo-electric film 106 is acoustically coupled to the exterior of the sensor tube 108 through contact of one face of the film 106 to the exterior of the sensor tube 108 and an applied pressure to the opposite side of the film 106 by a foam sheet 148 of selected thickness to provide the desired pressure of the film 106 against the exterior tube wall 146. The piezo-electric film 106 makes contact with at least a fraction of the circumference of the sensor tube 108 in one embodiment, and the piezo-electric film 106 makes contact with 180 degrees of the circumference of the sensor tube 108 in another embodiment. In additional embodiments where a higher sensitivity to sensing pressure waves within the sensor tube 108 is desired, the contact area is increased to include up to 360 degrees of the circumference of the sensor tube 108.

As shown in FIGS. 5A, 5B, 5C, and 5D, the design of the piezo-electric film 106 provides two distinct sound sensing elements 200, 202 on the front, spaced a selected distance apart 204 (e.g. 10.0 mm). Two sound sensing elements are used for reasons explained in U.S. Pat. No. 6,705,319. In an embodiment, the piezo-electric film 106 is polyvinylidene difluoride (PVDF), which exhibits a piezo-electric behavior at areas covered on both sides of the film by electrodes made of a conductive material, such as the non-limiting example of silver ink. By printing the conductive ink in selected regions, a single piece of film can contain one or more distinct sound pressure sensing elements. Using this method, two parallel electrode strips are printed on one side of the film to provide sound sensing elements 200, 202. On the opposite side of the film is printed one large negative polarity electrode 206 that covers at a minimum the area opposite the positive polarity electrodes comprising elements 200, 202.

To provide shielding against electromagnetic interference, the film 106 is folded into configuration 207 such that the negative polarity electrode 206 surrounds the exterior of the folded film. In this configuration, the positive electrodes 200, 202 are encapsulated within the sandwich of the two folded halves and the negative polarity electrode 206 functions as a shield against electromagnetic interference (EMI). The folded halves of the film are held together with a double sided tape, such as 3M 9460, in one embodiment.

The separation distance 204 between elements 200, 202 defines the time lag between sensing of acoustic pressure waves at elements 200, 202. The electrode surface area of each element defines the sensitivity of the film in detecting vibrations from sound pressure waves within the sensor tube 108. In further embodiments, electrode surface area is increased by increasing the element length 208 and/or the element width 210.

Electrical communication of the piezo-electric film electrodes to the amplifier circuitry comprises any number of lead attachment methods in one or more embodiments, including those disclosed by Measurement Specialties Incorporated in "Piezo Film Sensors Technical Manual."

An embodiment for lead attachment comprises a printed circuit board (PCB) 212 with holes 214 surrounded by plated conductive pads 216 on both sides of the PCB 212. A metal eyelet 218 (for example, Stimpson A3802) inserted through each PCB hole 214 and each piezo film hole 220 causes the plated conductive pads 216 on the top of the PCB to make electrical contact with the negative electrode 206 by way of the conductive eyelet 218 when the eyelet is crimped. The same metal eyelet 218 pulls the electrodes for elements 200, 202 to be in direct contact with the plated conduction pads 216 (not shown) on the bottom of the PCB 212. The signals from the electrodes for elements 200, 202 and 206 are connected through the PCB 212 to a miniature PCB mounted connector 222. The top of the PCB 212 is covered with a conductive plane connected to the negative electrode 206 in one embodiment to provide EMI shielding at the connection points between the PCB 212 and piezo film.

One embodiment using an array of two or more sensor elements provides a means to match the amplitude sensitivity of the elements to each other. After assembling and closing the device 100 as shown in FIG. 4, the mean backing pressure applied to sensor element 200, as shown in FIGS. 5A, 5B, 5C, and 5D, may be slightly different than the mean backing pressure applied to sensor element 202, which may lead to one sound sensing element having better acoustic coupling and a higher sensitivity compared to the other sound sensing element. In one embodiment, this difference can be accounted for computationally when processing the signals from each of these elements by multiplying one signal by a gain factor to normalize it to the other signal. In another embodiment, this difference can be minimized by modifying the mean pressure applied to one of the sensors until the sensitivities of both elements are substantially equal. One way of accomplishing this is to alter the pressure applied to the back of sensor element 200 with a set screw 300, as illustrated in FIG. 4, which causes deflection of a plate 302 that increases pressure on the back of the foam sheet 148 of element 200. With this configuration, the sound sensor elements 200 and 202 are matched by observing the acoustical signals from each element in response to an excitation pressure wave from the speaker 104 and turning the set screw 300 until their amplitudes are equal. In one embodiment, to ensure that the mean pressure on sensor element 202 is always more than that of sensor element 200 prior to adjusting the set screw, the support behind foam sheet 148 for sensor element 202 is configured to apply a higher initial pressure to element 202 compared to the initial pressure for element 200.

Referring back to FIG. 2, a further enhancement to improve matching of the frequency response between the sensor elements 200, 202 is to provide a symmetry of boundary conditions placed upon the sensor tube 108 to the left and right of each sensor element. For example, a left ring 304, center ring 306, and right ring 308 that come in contact with the piezo-electric film 106 and outside circumference of the sensor tube 108 provide low displacement boundary conditions proximally and distally to each sensor element with respect to the longitudinal axis of the tube 108. When a planar sound wave is propagating longitudinally in either direction inside the sensor tube lumen 144, the wall of the sensor tube 108 displaces radially in response to the changing pressures within. However, the amount of displacement is partly affected by the proximity of boundary conditions placed on the wall of the sensor tube 108. For example, in the absence of center ring 306, if the sound wave is propagating from left to right, the boundary condition of the tube wall at 304 will be approximately stationary so that the tube wall displacement at sensor element 200 may be less than the tube wall displacement at sensor element 202 because the displacement at element 200 may not reach the maximum possible displacement due to its close proximity to the stationary boundary condition at 304. To minimize this asymmetric behavior with regards to tube wall displacement at the sensor elements 200, 202, the contact rings 304, 306, and 308, provide symmetric stationary boundary conditions on either side of the sensor elements 200, 202 so that the radial displacement of the wall of the sensor tube 108 will be similar regardless of direction of sound propagation or sensor element location.

The present disclosure relates to a device for an acoustic reflectometer for use in air filled tubes as well as a reflectometer for use with liquid filled tubes such as catheters containing liquids such as blood, saline, water, or urine. Due to the unique design of the sensor tube 108 in combination with the sound sensing elements 200 and 202, the sound pressure waves produced within the liquid medium cause radial deflection of the tube wall 146 which is detected by the sound sending elements 200, 202.

Figure 6:
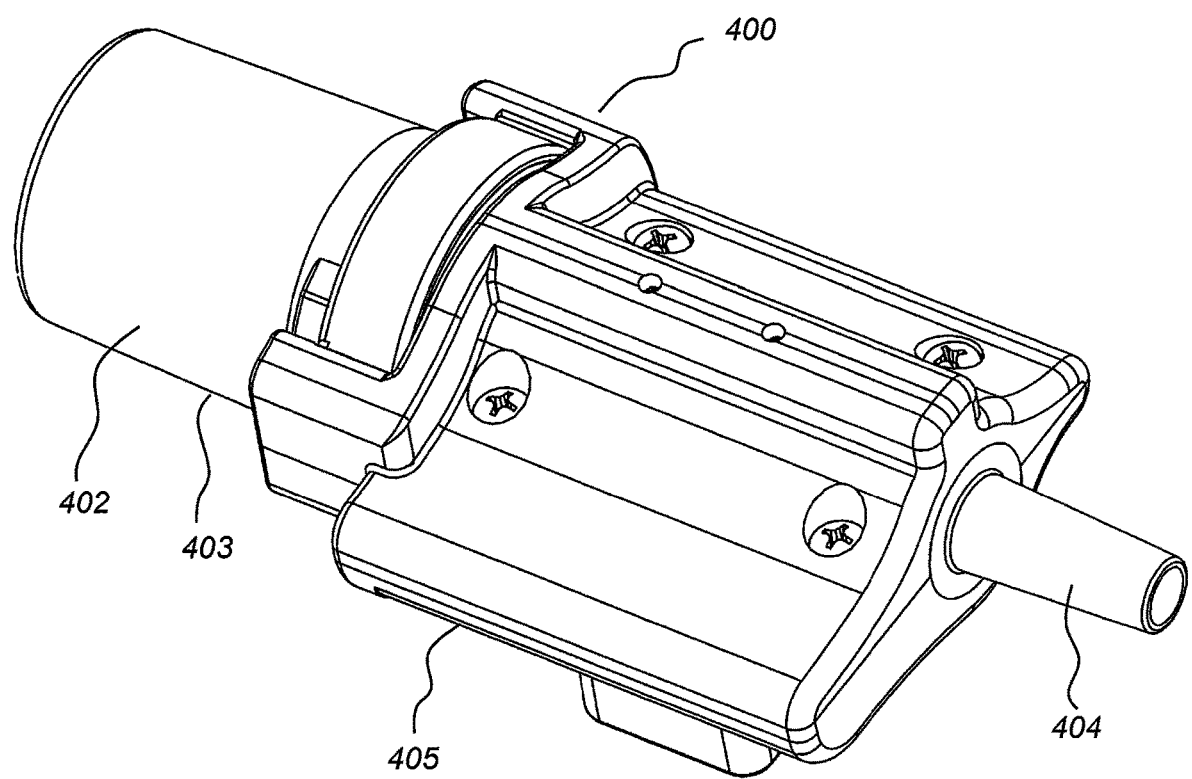
FIG. 6 illustrates a perspective view of an acoustic reflectometry device according to an embodiment of the present disclosure.

Referring now to FIG. 6, to reduce the length of the device for use in neonatal size ETTs, including those having IDs between 2.0 mm and 3.5 mm, the neonatal device 400 is provided. The neonatal device 400 includes a 15 mm airway device fitting 402 for connection to the breathing circuit and a nozzle 404 of specified inner diameter for connection to an endotracheal tube of the same specified inner diameter. The 15 mm airway device fitting 402 comprises a sound generating section 403, which is connected to a sound sensing section 405.

Figures 7A, 7B:
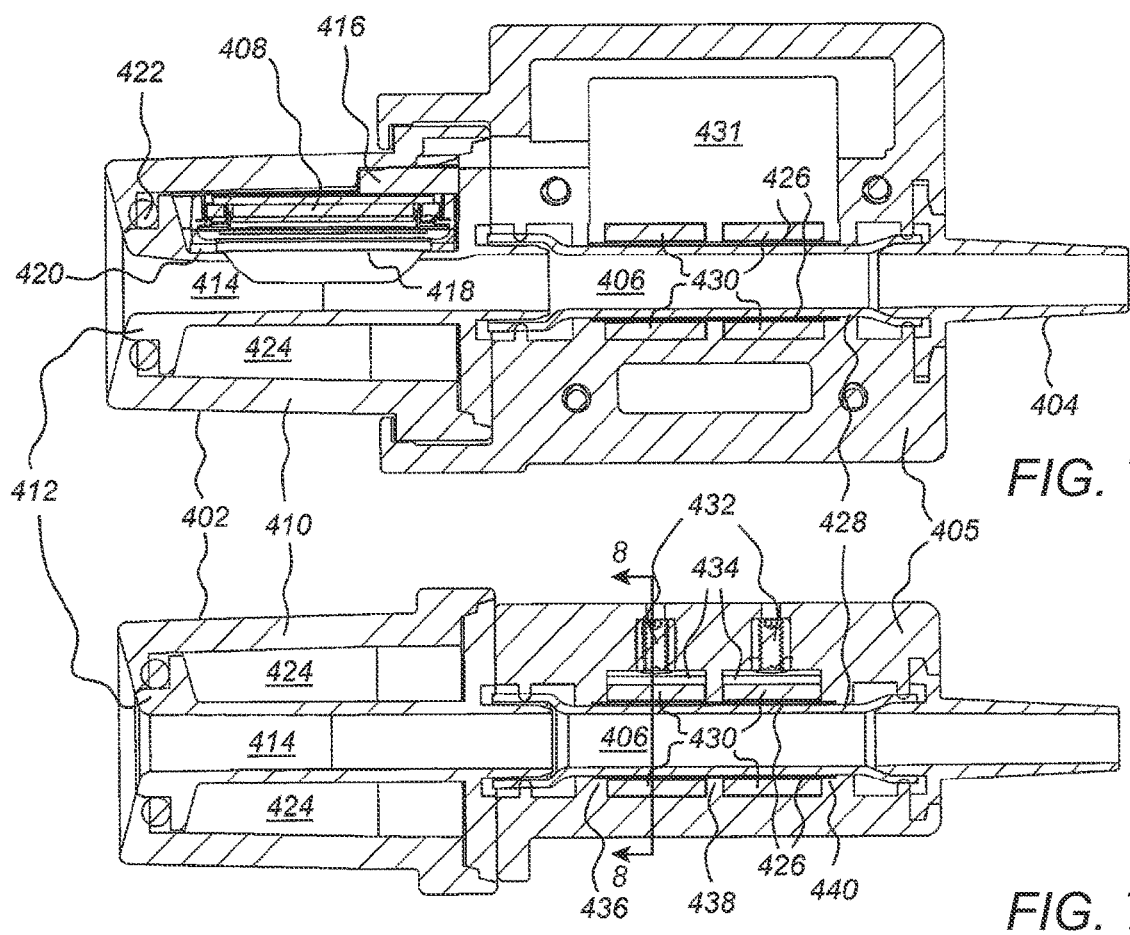
FIGS. 7A and 7B illustrate cross sectional views of an acoustic reflectometry device according to an embodiment of the present disclosure.

Referring to FIGS. 7A and 7B, the internal diameter of a sensor lumen 406 was selected as the largest of the neonatal size ETTs (3.5 mm ID) to provide a single sensor for all ETT sizes of 3.5 mm ID and less that presented a relatively low dead space and flow resistance. The small diameter of the sensor lumen 406 made it possible to place the speaker 408, for generating sound pulses, directly within the 15 mm airway device fitting 402. This modification resulted in decreasing the device length to 6.3 cm, which is only 3.3 cm longer than a standard 15 mm connector with nozzle.

The dead space volume for the device 400, which is important when considering how much air is being rebreathed by the patient, is approximately 0.6 cc. In comparison, a standard 15 mm connector with nozzle has a dead space of approximately 1.9 cc due largely to the contribution of the significant volume within the 15 mm airway device fitting.

The 15 mm airway device fitting 402 with integrated speaker design of one embodiment includes two primary parts, a 15 mm shell 410 and a speaker platform insert 412, which is configured to slide inside the shell 410. In an embodiment, the sound generating speaker 408 is configured to be coupled to the speaker section lumen 414 using the same method and components described above with regard to the embodiments of FIGS. 1-5. The speaker 408 with circuit board 416 are positioned onto the speaker platform insert 412 with a non-porous, compliant, thin membrane 418 and a rubber gasket 420 to provide a pressure seal between the speaker 408 and the device lumen 414. An O-ring 422 provides a pressure seal between the speaker platform insert 412 and the 15 mm shell 410.

The volume between the 15 mm shell 410 and the speaker platform insert 412 forms the speaker back cavity 424. The volume of the speaker back cavity 424 should be selected per the specification of the speaker manufacturer to provide the desired acoustical response from the speaker 408.

Figure 8:
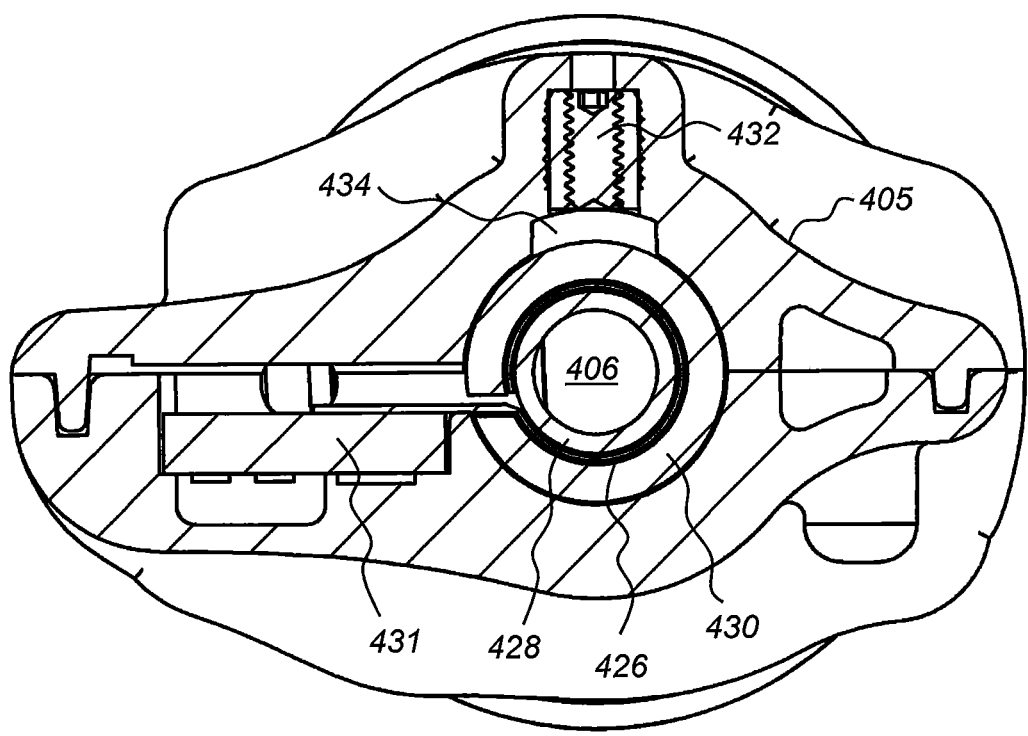
FIG. 8 illustrates a cross sectional view of an acoustic reflectometry device according to an embodiment of the present disclosure.
Figure 9A:
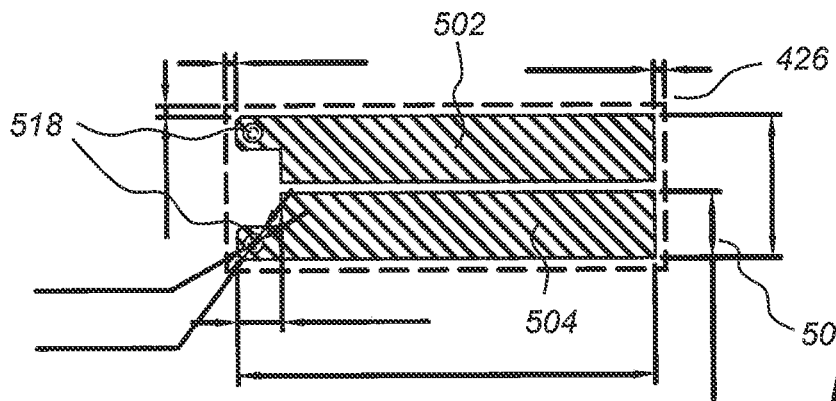
FIGS. 9A, 9B, 9C, and 9D illustrate plan views of sensors of acoustic reflectometry devices according to an embodiment of the present disclosure.
Figure 9B:
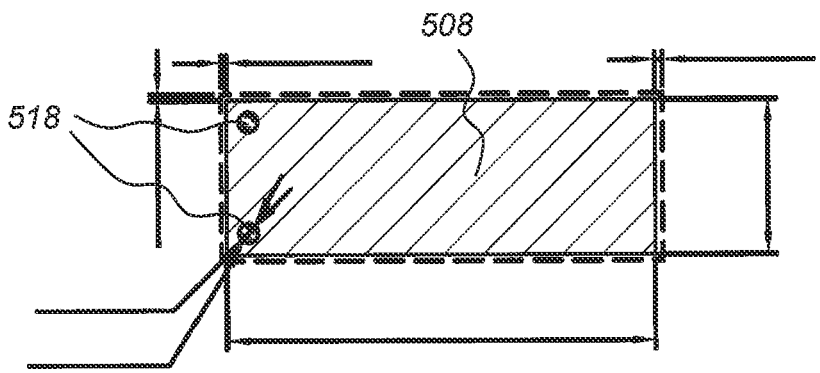
Figure 9C:
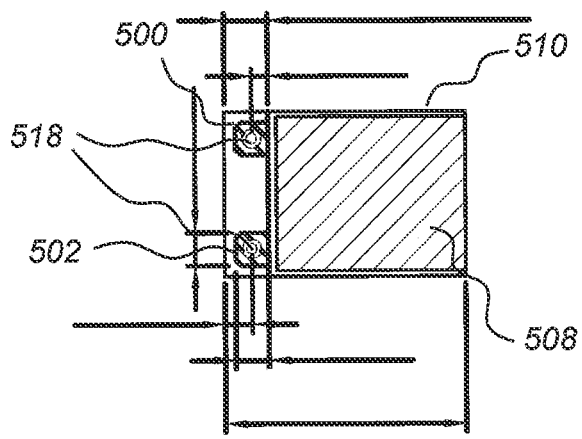
Figure 9D:
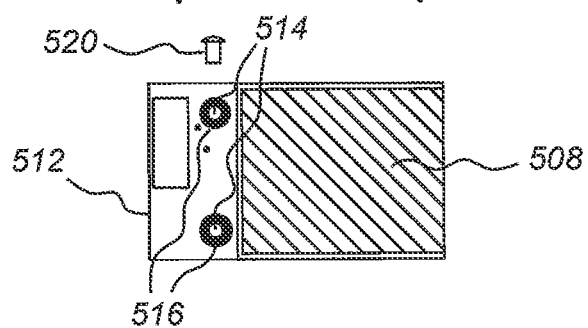

The sound sensing section 405 is configured in one embodiment to include one or more of the structures described above with regard to the embodiments of FIGS. 1-5. As shown in FIGS. 7A, 7B, and FIG. 8, a piezo-electric film 426 is acoustically coupled to the exterior of a sensor tube 428 through contact of one face of the film 426 to the exterior of the sensor tube 428 and an applied pressure to the opposite side of the film 426 by a foam sheet 430 of selected thickness to provide the desired pressure of the film 426 against the exterior wall of the tube 428. To provide a high sensitivity to sensing pressure waves within the sensor tube 428, the contact area includes 180 degrees of the circumference of the sensor tube 428 in one embodiment and up to 360 degrees of the circumference of the sensor tube 428 in additional embodiments.

The piezo-electric film 426 is connected to a PCB 431 which also provides a connection means for a cable to connect to the sound receiving amplifier circuitry. The PCB 431 provides a connection means between the speaker PCB 416 and a cable to connect to the sound generating amplifier circuitry in an embodiment. In an embodiment, the PCB 431 contains the sound generating and receiving amplifier circuitry, a power source such as a battery, and a wireless transceiver for communication with the processing unit.

As described above with regard to the embodiments of FIGS. 1-5, the embodiments of FIGS. 7A and 7B includes a mechanism to match the amplitude sensitivity of the sound sensing elements. For each sound sensing element, a set screw 432 causes deflection of a plate 434 which increases pressure on the back of a foam sheet 430 and the respective sound sensing element. With this configuration, the sound sensor elements can be matched by observing the acoustical signals from each element in response to an excitation pressure wave from the speaker 408 and turning the appropriate set screw 432 until their amplitudes are equal.

As described above with regard to the embodiments of FIGS. 1-5, symmetry of boundary conditions to the left and right of each sensor element are provided in an embodiment by a left ring 436, center ring 438, and right ring 440 that are in contact with the circumference of the piezo-electric film 426 and outside wall of the tube 428, as shown in FIGS. 7A and 7B.

As shown in FIGS. 9A, 9B, 9C, and 9D, the design of the neonatal sensor piezo-electric film 426 is similar to the design described above with regard to the embodiments of FIGS. 1-5 with several modifications to satisfy the user requirements for neonates.

Referring back to FIGS. 7A, 7B, and FIG. 8, due to the reduced contact area between the piezo-electric film 426 and the sensor tube 428 as a result of the smaller diameter sensor tube 428 as compared to device 100, the electrode width 506 for the sound sensing elements A and B 502, 504 was doubled to compensate for the reduced contact surface area. The increase in electrode width decreases the effective separation distance between the center lines of the two electrodes from 10 mm to 7 mm. This reduced distance reduces the lag time between sensing of acoustic pressure waves at the elements 502 and 504. A reduced lag time results in an increased cutoff frequency of the high pass behavior (differential filter effect) of using the difference between the signals sensed by two elements in a phased array to calculate the reflection response of a system. This trade-off of increased sensitivity in exchange for reduced lower frequency energy in the reflection response signal is acceptable because the acoustic reflections that arise from within the short neonatal airways contain a majority of energy in frequencies above those affected by the reduced lag time.

The electrodes for the sound sensing elements 502 and 504 are positive polarity and the large electrode 508 on the opposite side of the film is negative polarity. As described above with regard to the embodiments of FIGS. 1-5, the film 426 is folded into configuration 510 such that the negative polarity electrode 508 surrounds the exterior of the folded film.

The lead attachment configuration is identical to that described above with regard to the embodiments of FIGS. 1-5 using a PCB 512 with holes 514 surrounded by plated conductive pads 516 and the piezo film holes 518 held together with a metal eyelet 520 inserted through the holes 514 and 518.

Figure 10:
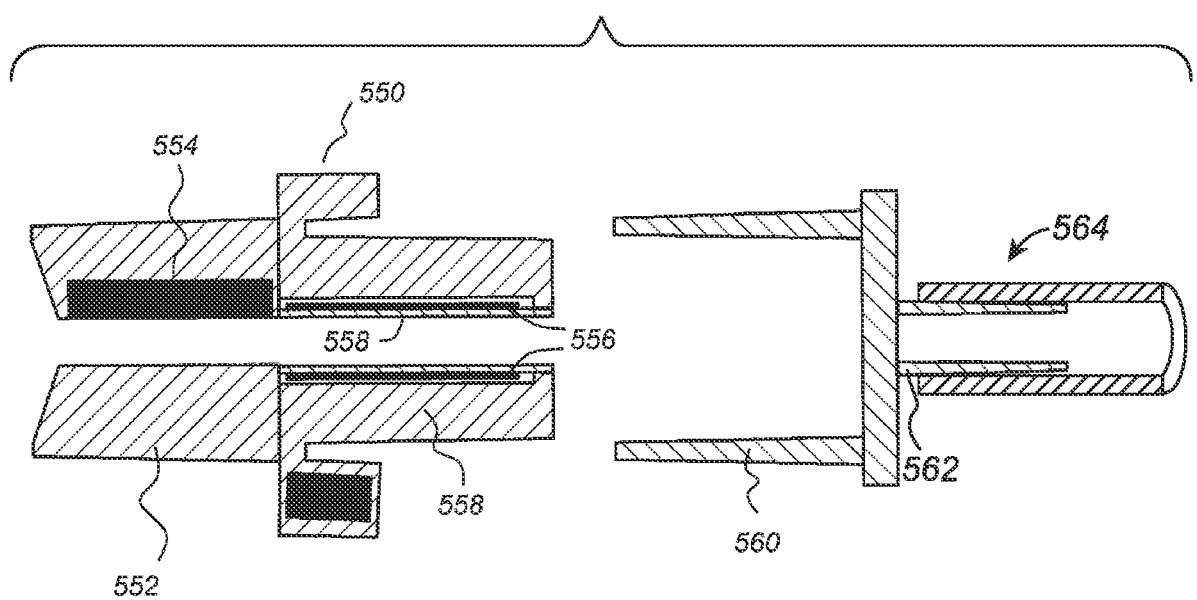
FIG. 10 illustrates a cross sectional view of an acoustic reflectometry device according to an embodiment of the present disclosure.

An embodiment for minimizing the length of the neonatal sensor is shown in FIG. 10. This embodiment includes a sensor 550 comprising a 15 mm airway device fitting 552 containing a sound generating component 554 and the sound sensing sensor film component 556 which is wrapped around the outside circumference of a compliant walled tube 558. The ETT adapter 560 is shaped on the inside to accept the sensor component 558 and maintain a pressure seal and has a nozzle 562 on the distal end to connect directly to an ETT. With this design, the sensor 550 can be easily removed from the breathing circuit if desired and a ventilator hose connected directly to the standard 15 mm airway device fitting on the adapter 560.

Figure 11:
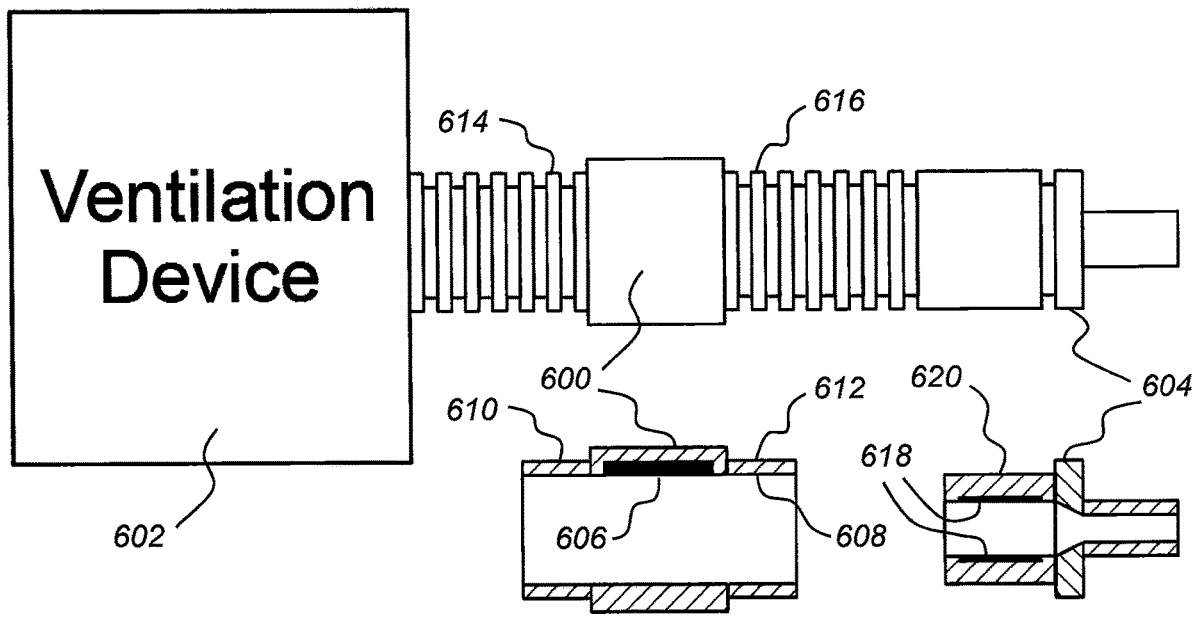
FIG. 11 illustrates a cross sectional view of an acoustic reflectometry device according to an embodiment of the present disclosure.

Another alternate embodiment for minimizing the length of the neonatal sensor is shown in FIG. 11. This configuration consists of a separate sound generating component 600 that is located in the breathing circuit anywhere between the ventilator 602 (including inside the ventilator) and the sensor component 604. The sound generating component 600 contains a sound generator 606 embedded in lumen wall 608. The sound generating component 600 may also have standard 22 mm hose fittings 610 and 612 on both sides to allow connection between ventilator hoses 614 and 616. The sensor film 618 is located within the 15 mm airway device fitting 620 which provides a sensor component that is about the same size as a standard 15 mm adapter. This configuration would yield a sensor with very low dead space volume (less than a standard 15 mm adapter), short length, and low weight. Alternately, the sound generator 600 can be fixed within the ventilator 602 which would provide the advantage of making it not part of the disposable breathing circuit components. Moving the sound generator 600 away from the patient will also reduce the sound pressure levels at the patient's ears if the sound generator 600 emits sound into the environment. This is particularly important for neonates where great care is taken to maintain a quiet environment for the patient.

In an embodiment, the sound generator 606 is contained within another in-line airway device such as a flow sensor, end-tidal C02 sensor, suction catheter system, heat moisture exchange filter, or humidifier.

For ETTs having an ID sized between 4.0 mm and 5.5 mm, similar embodiments to the neonatal acoustic reflectometry sensor in FIGS. 6-9 may be used with the difference being the inner diameter of the sensor lumen. A sensor lumen ID of 5.5 mm may be used with nozzles of specified ID for connection to ETTs having IDs between 4.0 mm and 5.5 mm in additional embodiments.

Figure 12:
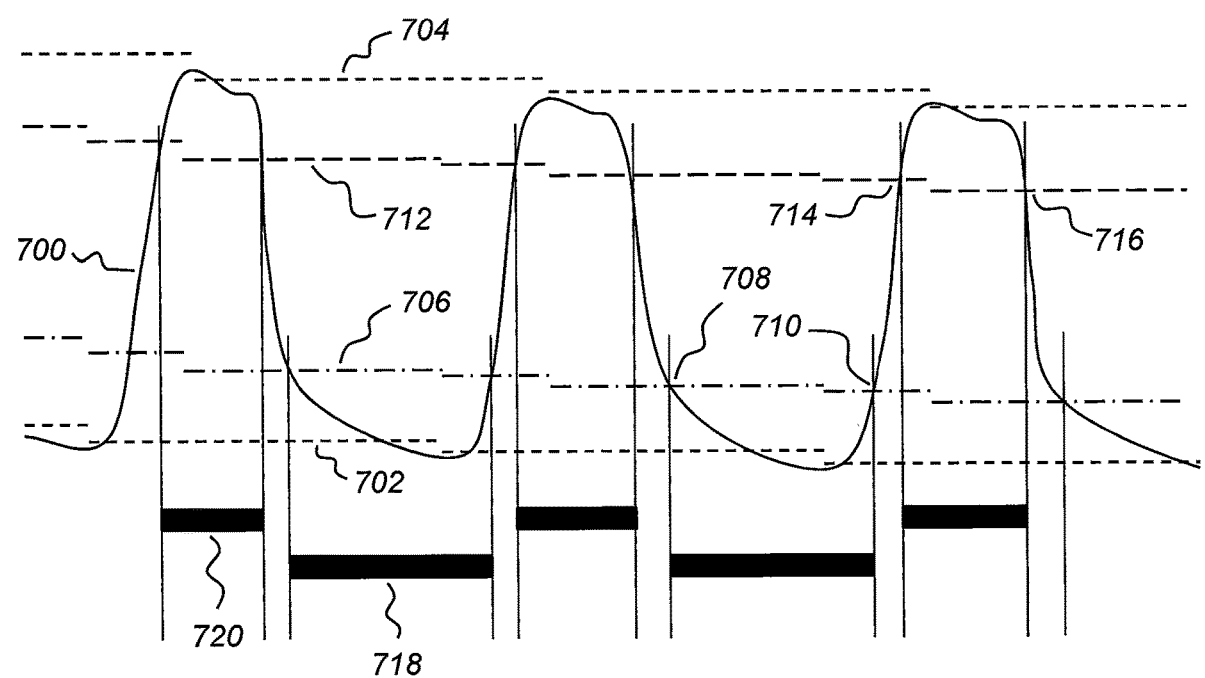
FIG. 12 illustrates a ventilator pressure waveform as recorded by a sensor of and acoustic reflectometry device according to an embodiment of the present disclosure.

Referring now to FIG. 12, the piezo-electric film of one or more embodiments of the present disclosure in the acoustic reflectometry sensor not only senses acoustical pressure waves from within the compliant tube, but with the appropriate filtering in the amplifier circuitry, the same film also senses the low frequency pressures generated within the breathing circuit by the ventilator. As shown in FIG. 12, a ventilation pressure waveform 700 sensed by the piezo-electric film may be used by a processor to synchronize collection of the acoustic reflectometry signals with a particular phase of the respiratory cycle. As one non-limiting example, due to the differences in acoustic reflectance of the airways that exist between end-inspiration and end-expiration, a technician or user selectively acquires the acoustic reflectometry signals during only one of the phases.

A method for synchronizing the collection of an acoustic reflectometry signal with a particular phase of the respiratory cycle includes maintaining moving averages over several respiratory cycles of the minimum ($\overline{P_{min}}$) 702 and maximum ($\overline{P_{max}}$) 704 sensed pressures in the ventilation pressure waveform 700 and establishing pressure thresholds, which define the beginning or end of a particular phase. As one non-limiting example, a minimum threshold 706 of $\overline{P_{min}}+0.2(\overline{P_{max}}-\overline{P_{min}})$ is used to identify the end of expiration 708 or onset of inspiration 710 and a maximum threshold 712 of $\overline{P_{min}}+0.8(\overline{P_{max}}-\overline{P_{min}})$ is used to identify the end of inspiration 714 or the onset of expiration 716. In an embodiment, once a particular phase has been identified by the algorithm, the CPU performs collection of the acoustic reflectometry signal during that phase. As one non-limiting example, the CPU selectively collects acoustic reflectometry signals only during the period 718 between end-expiration and the onset of inspiration. In a further embodiment, the CPU selectively collects acoustic reflectometry signals only during the period 720 between end-inspiration and the onset of expiration.

While the invention has been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. An apparatus for acoustically detecting a location of a tube in a body, comprising:
    a housing comprising an airway lumen sized for breathing gases for a ventilated patient, wherein the housing comprises a tube connector sized for connection to an endotracheal tube;
    a sound generator positioned in the housing to generate a sound signal in the airway lumen; and
    a sensor wrapped at least partially around a compliant tube positioned in the housing distally relative to the sound generator, wherein the compliant tube defines part of the airway lumen, and the sensor is configured to detect acoustic pressure waves in the airway lumen by sensing radial contractions and expansions of the compliant tube caused by the acoustic pressure waves.

2. The apparatus of claim 1, wherein the housing comprises a first housing member coupled to a second housing member by a dampening material, the sound generator is positioned in the first housing member, and the sensor and the compliant tube are positioned in the second housing member.

3. The apparatus of claim 1, wherein the sensor is wrapped at least around 180 degrees of a circumference of the compliant tube.

4. The apparatus of claim 1, wherein the sensor comprises a piezo-electric film coupled to an exterior of the compliant tube and first and second electrodes on the piezo-electric film, and the first and second electrodes are spaced apart from each other on the piezo-electric film by a separation distance providing a time lag between the acoustic pressure waves detected at the first and second electrodes.

5. The apparatus of claim 4, further comprising a set screw that is configured to move relative to the housing to adjust a pressure applied by the set screw to one of the first and second electrodes.

6. The apparatus of claim 4, further comprising a foam sheet behind the piezoelectric film and the first and second electrodes on the piezo-electric film, opposite the compliant tube, for support of the piezo-electric film and the first and second electrodes on the film.

7. The apparatus of claim 1, wherein the housing further comprises a tube connector sized for connection to a neonatal endotracheal tube, and the tube connector has an inner diameter no greater than about 3.5 mm.

8. The apparatus of claim 7, wherein the housing further comprises a device fitting sized for connection to a ventilation system, the sound generator is positioned within the device fitting, and the sensor is positioned distally relative to the device fitting.

9. The apparatus of claim 1, further comprising a compliant non-porous membrane between the sound generator and the airway lumen.

10. The apparatus of claim 1, wherein the compliant tube has a wall thickness between 0.5 mm and 1.0 mm and the wall of the compliant tube has a material hardness of about Shore 35A durometer.

11. An apparatus for acoustically detecting a location of a tube in a body, comprising:
    a housing comprising an airway lumen sized for breathing gases for a ventilated patient;
    a sound generator positioned in the housing to generate a sound signal into the airway lumen;
    a sensor positioned in the housing distally relative to the sound generator, wherein the sensor comprises first and second electrodes spaced apart by a separation distance that provides a time lag between acoustic pressure waves detected at the first and second electrodes;
    a compliant tube positioned in the housing distally relative to the sound generator to define part of the airway lumen, wherein the compliant tube is aligned with the sensor, the sensor is configured to detect the acoustic pressure waves in the airway lumen by sensing radial contractions and expansions of the compliant tube caused by the acoustic pressure waves, and the sensor comprises a film that is coupled to an exterior of the compliant tube and the first and second electrodes are supported on the film; and
    a ring, extending around the compliant tube, in contact with the film between the first and second electrodes to provide a boundary condition for the sensor.

12. The apparatus of claim 11, wherein the film comprises a piezo-electric film.

13. The apparatus of claim 11, further comprising a set screw configured to move relative to the housing to adjust a mean pressure applied by the set screw to one of the first and second electrodes to match an amplitude sensitivity of the first and second electrodes.

14. The apparatus of claim 13, further comprising an adjustment plate, wherein rotation of the set screw in a first rotational direction deflects the adjustment plate toward the one of the first and second electrodes.

15. The apparatus of claim 11, wherein the sensor is wrapped at least partially around the compliant tube.

16. The apparatus of claim 11, wherein the housing comprises a cavity behind the sound generator, opposite the airway lumen, for acoustic response of the sound generator, and the apparatus further comprises a shunt between the cavity and the airway lumen with a compliant barrier across the shunt.

17. An apparatus for acoustically detecting a location of a tube in a body, comprising:
    a sound generator to generate a sound signal into an airway lumen sized for breathing gases for a ventilated patient;
    a compliant tube positioned distally relative to the sound generator and defining part of the airway lumen;
    a sensor positioned distally relative to the sound generator, wherein the sensor comprises a film coupled to an exterior of the compliant tube, the sensor comprises first and second electrodes spaced apart from each other on the film by a separation distance providing a time lag between acoustic pressure waves detected at the first and second electrodes, wherein the sensor is configured to detect acoustic pressure waves in the airway lumen by sensing radial contractions and expansions of the compliant tube caused by the acoustic pressure waves; and a housing including the sensor, the compliant tube, and a tube connector sized for connection to an endotracheal tube.

18. The apparatus of claim 17, wherein the film comprises a piezo-electric film.

19. The apparatus of claim 17, wherein the sound generator is positioned within the ventilator, the apparatus further comprises a hose configured to be coupled in line between the ventilator and the housing, and the housing further comprises a connector for connecting to a distal end of the hose.

20. The apparatus of claim 17, further comprising:
   a first ring, extending around the compliant tube, in contact with a first end of the film to provide a first boundary condition for the sensor;
   a second ring extending around the compliant tube, in contact with the film and positioned between the first electrode and the second electrode, the second ring providing a second boundary condition for the sensor; and
   a third ring, extending around the compliant tube, in contact with a second end of the film to provide a third boundary condition for the sensor.

* * * * *